United States Patent

Cinberg et al.

Patent Number: 5,207,685
Date of Patent: May 4, 1993

[54] TYMPANIC VENTILATION TUBE AND RELATED TECHNIQUE

[76] Inventors: James Z. Cinberg, 167 N. Ridgewood Rd., South Orange, N.J. 07079; Peter J. Wilk, 185 W. End Ave., New York, N.Y. 10023

[21] Appl. No.: 921,308

[22] Filed: Jul. 28, 1992

Related U.S. Application Data

[63] Continuation-in-part of Ser. No. 833,511, Feb. 11, 1992.

[51] Int. Cl.⁵ ............................................. A61F 17/00
[52] U.S. Cl. ........................................ 606/109; 606/1; 606/108; 606/167; 606/170
[58] Field of Search ............... 606/1, 108, 109, 167, 606/170, 180; 623/10; 604/264

[56] References Cited

U.S. PATENT DOCUMENTS

| | | | |
|---|---|---|---|
| 3,530,860 | 9/1970 | Majoros | 606/109 |
| 3,871,380 | 3/1975 | Heros. | |
| 3,888,258 | 6/1975 | Akiyama. | |
| 3,948,271 | 4/1976 | Akiyama | 606/109 |
| 3,982,545 | 9/1976 | Silverstein. | |
| 4,168,697 | 9/1979 | Cantekin. | |
| 4,764,168 | 8/1988 | Suh. | |
| 4,775,370 | 10/1988 | Berry. | |
| 4,971,076 | 11/1990 | Densort et al. | 606/109 |
| 5,026,378 | 6/1991 | Goldsmith. | |
| 5,047,053 | 9/1991 | Jahn. | |
| 5,053,040 | 10/1991 | Goldsmith | 606/109 |

FOREIGN PATENT DOCUMENTS

1326276  7/1987  U.S.S.R. .

Primary Examiner—David M. Shay
Assistant Examiner—Glenn K. Dawson
Attorney, Agent, or Firm—R. Neil Sudol; Henry D. Coleman

[57] ABSTRACT

A tympanic ventilation tube for ventilating and/or releasing fluid from the middle ear has, in accordance with the present invention, a tubular member and a first flange and a second flange connected to opposite ends of the tubular member. The first flange is provided with a cutting edge and with a tongue extension angularly spaced from the cutting edge. The cutting edge facilitates the incising of the tympanic membrane during the insertion of the tubular member, while the first flange and the second flange seat against opposite sides of the membrane following the insertion.

21 Claims, 3 Drawing Sheets

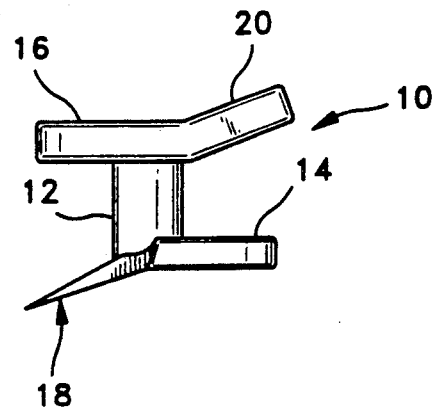
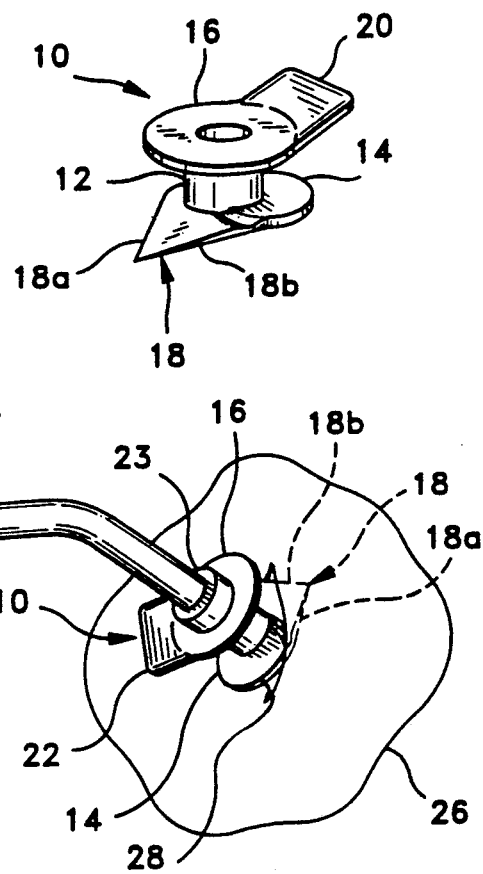
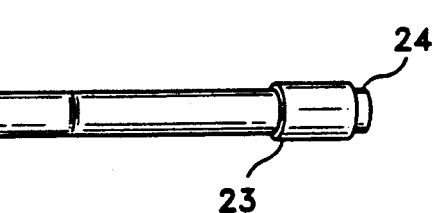
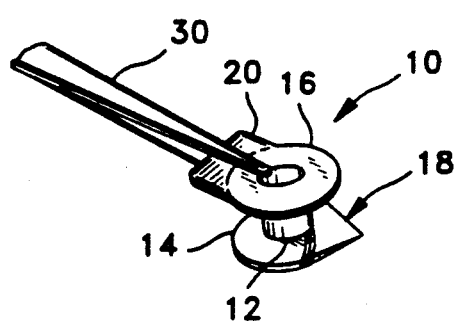
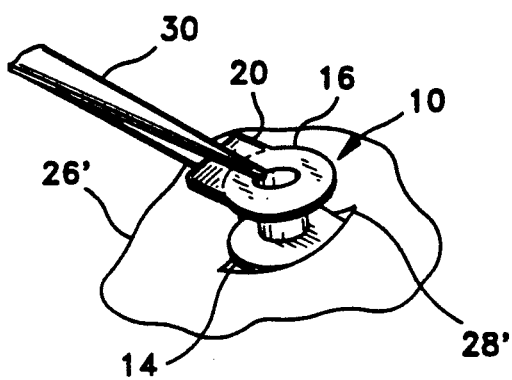

TYMPANIC VENTILATION TUBE AND RELATED TECHNIQUE

CROSS REFERENCE TO RELATED APPLICATION

This application is a continuation-in-part of application Ser. No. 833,511 filed Feb. 11, 1992 pending.

BACKGROUND OF THE INVENTION

This invention relates to a ventilation tube which is placed in a patient's tympanic membrane for purposes of pressure equalization between between the middle ear cleft and the ambient atmospheric pressure and also for draining fluid from the middle ear. In addition, this invention relates to an associated surgical technique.

Children frequently have an abnormal condition characterized by fluid in the middle ear cleft. A myringotomy or tympanostomy with placement of a ventilation or pressure equalization tube is a surgical operation performed on the ear drum to drain the fluid and ventilate the middle ear for a longer period than would be possible with only an incision of the ear drum as spontaneous drum closure occurs in a week or two after the incision of the ear drum: a result of standard repair processes of an incised ear drum. During a myringotomy and tube placement, as conventionally performed, an ear knife cuts the ear drum and creates an incision. Complications of this procedure are inadvertant laceration of the external ear canal as the knife moves towards or away from the drum and creation of a drum incision which is either too short or too long. Then a ventilation tube is inserted through the incision and manipulated to remain seated in the incision, thereby providing a duct or channel for draining fluid from the middle ear and ventilating the middle ear space via the external auditory canal.

During insertion down into the external auditory canal and placement in the tympanic membrane, the ventilation tube is held by a special grasping forceps. Because the ventilation tube is so tiny and the ear drum so delicate, a myringotomy and tube placement is an especially sensitive operation and gives rise to considerable challenges to a surgeon's dexterity and patience.

OBJECTS OF THE INVENTION

An object of the present invention is to provide an improved ventilation or pressure equalization tube for use in ventilating and/or draining fluid from the middle ear.

A related object of the present invention is to provide an improved method for performing a myringotomy.

Another, more particular, object of the present invention is to provide a myringotomy method which is easier, quicker and more economical than conventional procedures.

An even more particular object of the present invention is to provide an implant that can both incise the ear drum and serve as a pressure equalization device.

These and other objects of the present invention will be apparent from the descriptions and illustrations herein.

SUMMARY OF THE INVENTION

A tympanic ventilation or pressure equalization tube for the middle ear comprises, in accordance with the present invention, a tubular member with a first, proximal flange and a second, distal flange connected to opposite ends of the tubular member. The first flange remains outside the middle ear, while the second flange is seated deep to the ear drum, upon placement of the ventilation tube in an incision in the ear drum. The first flange is provided with a cutting edge and with a tongue extension angularly spaced from the cutting edge. The cutting edge facilitates the incising of the tympanic membrane during the insertion of the tubular member.

According to another feature of the present invention, the tongue extension projects from the first flange on a side thereof displaced approximately 90° from the cutting edge. The first flange may be provided with an additional tongue extension projecting from the first flange on a side thereof displaced approximately 180° from the cutting edge.

According to a further feature of the present invention, at least part of the second flange is flexible and may be conformed with a tongue extension. Preferably, the tongue extension is rigid to facilitate insertion through an incision in a tympanic membrane.

A method for ventilating and/or releasing fluid from the middle ear comprises, in accordance with the present invention, the steps of (a) providing a tympanic ventilation tube having a first flange at one end and a second flange at an opposite end, the first flange being provided with a cutting edge, (b) pressing the cutting edge against a tympanic membrane so as to form a perforation in the membrane, (c) removing the cutting edge from the perforation, and (d) introducing the second flange through the perforation, while maintaining the first flange on an outer side of the tympanic membrane, thereby seating the tube in the tympanic membrane.

Pursuant to another feature of the present invention, where the tube includes a tongue extension which is connected to the first flange and which is 90° offset from the cutting edge, the step of introducing includes the steps of grasping this tongue extension and manipulating the ventilation tube via this tongue extension to insert the second flange through the perforation.

Where the tube includes a tongue extension which is connected to the first flange and which is 180° offset from the cutting edge, the step of pressing may include the steps of grasping this tongue extension and manipulating the ventilation tube via this tongue extension to incise the tympanic membrane with the cutting edge. In that event, the tongue extension is advantageously positioned on a side of the first flange opposite the cutting edge, i.e., displaced approximately 180° from the cutting edge, to transmit pressure to the cutting edge.

According to another feature of the present invention, the second or distal flange is provided with a tongue extension, the step of introducing including the step of first inserting the tongue extension through the perforation and subsequently inserting the second flange through the perforation. Preferably, the tongue extension on the second or distal flange is 180° opposed to a tongue extension on the first or proximal flange. The latter tongue extension is grasped via a forceps to insert the tongue extension on the distal flange through the incision in the ear drum.

Where part of all of the second flange is flexible, the method further comprises the step of bending the second flange against the tympanic membrane during the step of pressing.

A myringotomy ventilation tube represents a considerable advance. A myringotomy and tube placement can be performed more quickly, more safety and with greater ease, inasmuch as the incision and ventilation tube insertion steps are performed by the same instrumentation, namely, the ventilation tube itself.

This technique in accordance with the present invention results in considerable savings inasmuch as reusable or disposable ear drum knives are no longer needed. Such knives are resterilized and stored or thrown away, respectively, after a single operation. Although the ventilation tube in accordance with the invention will be more expensive than a conventional ventilation tube, it is expected that a cost saving will still accrue.

BRIEF DESCRIPTION OF THE DRAWING

FIG. 1 is side elevational view, on a substantially enlarged scale, of an implant or ventilaton tube for use in incising an ear drum in a myringotomy operation and for subsequently serving as a pressure equalization device.

FIG. 2 is a perspective view, on an enlarged scale, of the ventilation tube of FIG. 1.

FIG. 3 is a perspective view, also on an enlarged scale, of the ventilation tube of FIG. 1 connected to the distal end of an applicator rod.

FIG. 4 is a side elevational view, on an enlarged scale, of the applicator rod of FIG. 3, showing a nose extension for releasably coupling the ventilation tube to the application rod.

FIG. 5 is a perspective view, on an enlarged scale, of the ventilation tube of FIGS. 1-3, showing a grasping forceps holding the ventilation tube.

FIG. 6 is a perspective view, on an enlarged scale, of the ventilation tube and grasping forceps of FIG. 5, showing placement or removal of the ventilation tube from an incision formed in an ear drum.

DETAILED DESCRIPTION

Figure 7:
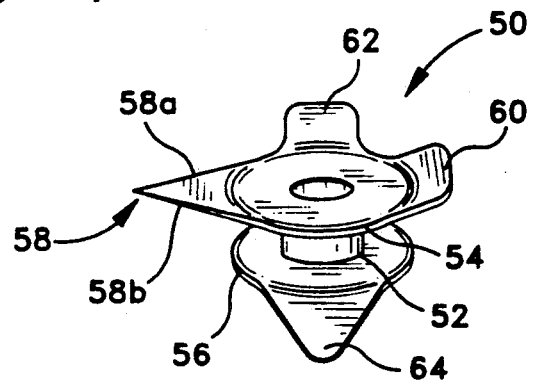
FIG. 7 is a schematic perspective view of another tympanic ventilation or pressure equalization tube with an integral incising edge, in accordance with the present invention.

As illustrated in FIGS. 1 and 2, a ventilation tube 10 for use in performing a myringotomy and subsequent pressure equalization comprises a tubular member 12, a first flange or collar 14 connected to a distal end of the tubular member, and a second flange or collar 16 connected to a proximal end of the tubular member. Distal flange 14 is provided along a distal side, i.e., on a side opposite proximal flange 16, with a cutting edge 18 comprising a pair of straight edge segments 18a and 18b oriented at an acute angle with respect to one another to form a cutting wedge extending in a direction away from proximal flange 16.

Ventilation tube 10 further comprises a non-cutting tongue or extension 20 connected to proximal flange 16. Tongue extension 20 projects at a shallow angle from proximal flange 16 on a side thereof opposite distal flange 14.

As depicted in FIG. 3, an elongate applicator rod or obturator 22 is removably coupled to ventilation tube 10 prior to the commencement of a myringotomy. As illustrated in FIG. 4, applicator rod 22 is formed at a distal end with a collar 23 and a distally extending nose portion 24 for releasably holding ventilation tube 10. Nose portion 24 may be inserted into ventilation tube 10 in a loose friction fit.

Applicator rod 22 is made of a material such as a metal or alloy having a limited malleability. Thus, applicator rod 22 may be bent, as shown in FIG. 3, for example, to assume a different configuration prior to the insertion of the rod and ventilation tube 10 into the external auditory canal of a patient. The malleability of applicator rod 22 facilitates the disposition of ventilation tube 10 at an appropriate place in the patient's tympanic membrane.

Ventilation tube 10 can have different dimensions and still be effective for seating in a patient's tympanic membrane.

In one configuration, flanges 14 and 16 are approximately three millimeters in diameter, while tubular member 12 has an inner diameter of approximately 1.25 millimeters. Flanges 14 and 16 are spaced from one another by a distance approximately equal to the thickness of a tympanic membrane, for example, approximately 1.55 millimeters.

It is to be noted that applicator rod 22 may be used with conventional ventilation tubes, for example, tubes with flanges or collars, but without cutting edge 18 or tongue extension 20. In such a case, the incision in the patient's tympanic membrane is formed conventionally, with a knife prior to the insertion of the ventilation tube.

In using tympanic ventilation tube 10 and applicator rod 22, ventilation tube 10 is first mounted to the distal end of applicator rod 22. Applicator rod 22 is then manipulated to insert ventilation tube 10 through the patient's auditory canal and to press cutting edge 18 against the tympanic membrane 26 (FIG. 3) so as to form a perforation or incision 28 (FIG. 3) therein. Preferably, upon achieving contact between ventilation tube 10 and the tympanic membrane, applicator rod 22 and concomitantly ventilation tube 10 are pressed towards the drum to facilitate the penetration of the tympanic membrane by cutting edge 18.

Upon penetration of cutting edge 18 through the tympanic membrane 26 to form perforation 28, applicator rod 22 is manipulated to insert distal flange 14 through the perforation, while maintaining proximal flange 16 on the outside of the tympanic membrane. Upon the seating of ventilation tube 10 so that distal flange 14 and proximal flange 16 are disposed on opposite sides of the tympanic membrane, nose portion 24 of applicator rod 22 is removed from ventilation tube 10.

It is to be noted that ventilation tube 10 ma be inserted with instrumentation other than applicator rod 22. For example, as depicted in FIGS. 5 and 6, a grasping forceps 30 may be used to press ventilation tube 10 against tympanic membrane 26', to incise perforation 28,, to insert distal flange 14 through the perforation or incision, and to seat ventilation tube 10 in the incision. Alternatively, another instrument (not illustrated) which may be used to perform these steps has an inner tube with a distal end insertable into tubular member 12 and further has an outer tube coaxially surrounding the inner tube and slidable in a distal direction with respect thereto to eject ventilation tube 10 from the distal end of the inner tube upon seating of the ventilation tube in the ear drum.

As illustrated in FIG. 7, another tympanic ventilation or pressure equalization tube 50 for ventilating and/or releasing fluid from the middle ear comprises a tubular member 52 provided with a first or proximal flange 54 and a second or distal flange 56 connected to opposite ends of tubular member 52. Proximal flange 54 is provided with a cutting edge 58 comprising a pair of straight edge segments 58a and 58b oriented at an acute angle with respect to one another to form a cutting wedge extending in a lateral or transverse direction away from proximal flange 54.

Figure 8A:
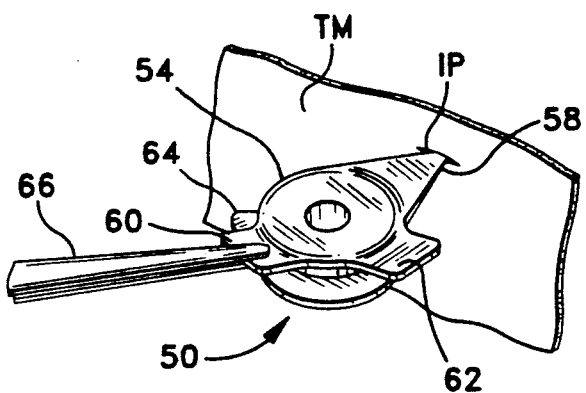
FIGS. 8A-8E are schematic perspective views depicting successive steps in the use of the tympanic ventilation or pressure equalization tube of FIG. 7.
Figure 8B:
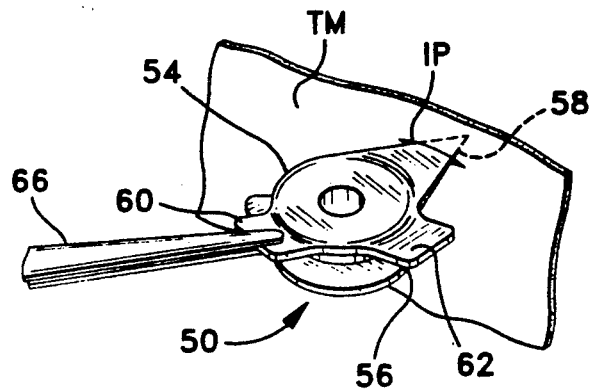
Figure 8C:
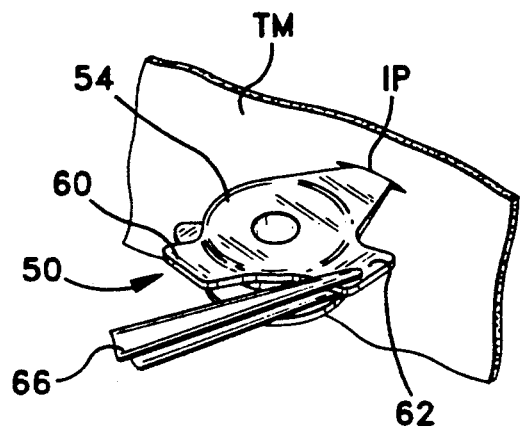
Figure 8D:
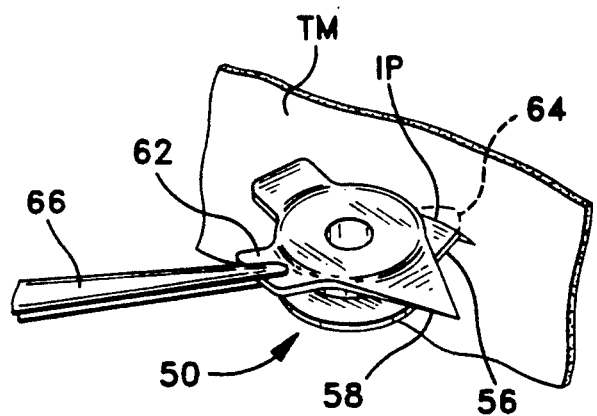
Figure 8E:
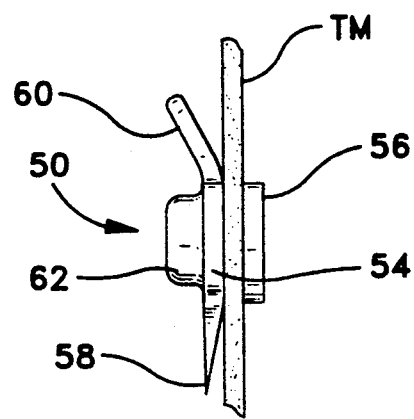

Proximal flange 54 is further provided with a first tongue extension 60 angularly spaced 180° from cutting edge 58 and a second tongue extension 62 angularly spaced 90° from cutting edge 58. Extension 60 facilitates grasping the device to apply pressure through cutting edge 58 to incise the tympanic membrane TM (FIGS. 8A-8E) during an insertion of tubular member 52, while proximal flange 54 and distal flange 56 seat against opposite sides of the membrane following the insertion, as illustrated in FIG. 8E.

Preferably, at least part of distal flange 56 is flexible for facilitating incising and insertion operations, described in detail hereinafter with reference to FIGS. 8A-8E. Flange 56 is also provided with a preferably rigid tongue extension 64 which facilitates insertion of distal flange 56 through an incision or perforation IP (FIGS. 8A-8E) formed in tympanic membrane TM.

In utilizing the tympanic ventilation or pressure equalization tube of FIG. 7 for ventilating and/or releasing fluid from the middle ear, cutting edge 58 is pressed against tympanic membrane TM so as to form incision IP in the membrane. To that end, a grasping forceps 66 is manipulated by the ear surgeon to clamp tongue extension 60 and to incise membrane TM, as illustrated in FIGS. 8A and 8B. FIG. 8B shows a later stage in the incising procedure, wherein distal flange 56 bends against tympanic membrane TM in response to the pressure exerted by the surgeon.

Upon formation of incision or perforation IP, tongue extension 60 is released, thereby temporarily leaving the ventilation tube held in membrane TM by cutting edge 58. Forceps 66 is then manipulated to grasp tongue extension 62, as illustrated in FIG. 8C, and to pull the ventilation tube in the proximal direction to remove cutting edge 58 from perforation IP. Ventilation tube 50 may then be rolled against tympanic membrane at that juncture to pivot the tube relative to forceps 66 so that forceps 66 grasp tongue extension 62 at the angle illustrated in FIG. 8D.

Alternatively, upon formation of incision or perforation IP, tongue extension 60 is used to pull cutting edge 58 from incision IP and to place ventilation tube 50 upon tympanic membrane TM. Forceps 66 is then manipulated to grasp tongue extension 62 at the angle illustrated in FIG. 8D.

Upon the removal of cutting edge 58 from incision IP and the grasping of tongue extension 62 at a suitable angle, forceps 66 is used to move tongue extension 64 of distal flange 56 through incision IP (FIG. 8D), while maintaining proximal flange 54 on an outer side of tympanic membrane TM to thereby dispose the tube in the membrane so that flanges 54 and 56 are seated against opposite sides of membrane TM, as illustrated in FIG. 8E. During the insertion of distal flange 56 through incision IP, that flange may distort slightly, owing to its inherent flexibility, to facilitate the insertion procedure.

The tympanic ventilation or pressure equalization tube of FIG. 7 and the associated method described above with reference to FIGS. 8A-8E serve to place the cutting edge 58 on the outer side o tympanic membrane TM, thereby reducing the chances of possible damage to organs of the middle ear.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that proximal flange 54 may be provided with only one tongue extension, rather than two. The one tongue extension may be located essentially at any angle with respect to cutting edge 58. Accordingly, it is to be understood that the drawings and descriptions herein are proffered by way of example to facilitate comprehension of the invention and should not be construed to limit the scope thereof.

What is claimed is:

1. A method for ventilating and/or releasing fluid from the middle ear, comprising the steps of:
    providing a tympanic ventilation tube having a first flange at one end and a second flange at an opposite end, said first flange being provided with a cutting edge;
    pressing said cutting edge against a tympanic membrane so as to form a perforation in said membrane;
    removing said cutting edge from said perforation; and
    introducing said second flange through said perforation, while maintaining said first flange on an outer side of said tympanic membrane, thereby seating said tube in said tympanic membrane.

2. The method defined in claim 1 wherein said tube includes a tongue extension connected to said first flange, said step of introducing including the steps of grasping said tongue extension and manipulating said ventilation tube via said tongue extension to insert said second flange through said perforation.

3. The method defined in claim 2 wherein said tongue extension projects from said first flange on a side thereof displaced approximately 90° from said cutting edge.

4. The method defined in claim 2 wherein said step of grasping is implemented via a grasping forceps.

5. The method defined in claim 1 wherein said tube includes a tongue extension connected to said first flange, said step of pressing including the steps of grasping said tongue extension and manipulating said ventilation tube via said tongue extension to incise the tympanic membrane with said cutting edge.

6. The method defined in claim 5 wherein said tongue extension projects from said first flange on a side thereof displaced approximately 180° from said cutting edge.

7. The method defined in claim 5 wherein said step of grasping is implemented via a grasping forceps.

8. The method defined in claim 1 wherein said second flange is provided with a tongue extension, said step of introducing including the step of first inserting said tongue extension through said perforation and subsequently inserting a body portion of said second flange through said perforation.

9. The method defined in claim 1 wherein at least part of said second flange is flexible, further comprising the step of bending said second flange against the tympanic membrane during said step of pressing.

10. A tympanic ventilation tube for releasing fluid from the middle ear, comprising:
    a tubular member;
    a first flange connected to one end of said tubular member, said first flange being provided with a cutting edge and with a tongue extension angularly spaced from said cutting edge; and a second flange connected to an opposite end of said tubular member, said cutting edge facilitating the incising of the tympanic membrane during the insertion of the tubular member, wherein said first flange and said second flange seat against opposite sides of the membrane following the insertion.

11. The tube defined in claim 10 wherein said tongue extension projects from said first flange on a side thereof displaced approximately 90° from said cutting edge.

12. The tube defined in claim 11 wherein said first flange is provided with an additional tongue extension projecting from said first flange on a side thereof displaced approximately 180° from said cutting edge.

13. The tube defined in claim 12 wherein said second flange is provided with a tongue extension.

14. The tube defined in claim 13 wherein at least part of said second flange is flexible.

15. The tube defined in claim 11 wherein said second flange is provided with a tongue extension.

16. The tube defined in claim 11 wherein at least part of said second flange is flexible.

17. The tube defined in claim 10 wherein said tongue extension projects from said first flange on a side thereof displaced approximately 180° from said cutting edge.

18. The tube defined in claim 17 wherein said second flange is provided with a tongue extension.

19. The tube defined in claim 17 wherein at least part of said second flange is flexible.

20. The tube defined in claim 10 wherein said second flange is provided with a tongue extension.

21. The tube defined in claim 10 wherein at least part of said second flange is flexible.

* * * * *